United States Patent [19]

Akashi et al.

[11] Patent Number: 5,166,345
[45] Date of Patent: Nov. 24, 1992

[54] PHOTOCHROMIC COMPOUND

[75] Inventors: Ryojiro Akashi, Otsu; Takashi Taniguchi, Yasu, both of Japan

[73] Assignee: Toray Industries, Inc., Tokyo, Japan

[21] Appl. No.: 742,079

[22] Filed: Aug. 7, 1991

Related U.S. Application Data

[60] Continuation of Ser. No. 495,599, Mar. 19, 1990, abandoned, which is a division of Ser. No. 151,601, Feb. 2, 1988, abandoned.

[30] Foreign Application Priority Data

| | | |
|---|---|---|
| Feb. 2, 1987 [JP] | Japan | 62-20379 |
| Feb. 13, 1987 [JP] | Japan | 62-29703 |
| Apr. 9, 1987 [JP] | Japan | 62-87607 |
| Jun. 9, 1987 [JP] | Japan | 62-144461 |
| Aug. 17, 1987 [JP] | Japan | 62-204574 |
| Dec. 8, 1987 [JP] | Japan | 62-311635 |
| Dec. 22, 1987 [JP] | Japan | 62-326498 |

[51] Int. Cl.$^5$ .......................... C07D 265/00
[52] U.S. Cl. .................................... 544/71
[58] Field of Search ........................... 544/71

[56] References Cited

U.S. PATENT DOCUMENTS

| | | | |
|---|---|---|---|
| 4,637,698 | 1/1987 | Kwak et al. | 544/71 |
| 4,720,547 | 1/1988 | Kwak et al. | 544/71 |
| 4,929,693 | 5/1990 | Akashi et al. | 526/259 |

FOREIGN PATENT DOCUMENTS

| | | | |
|---|---|---|---|
| 63-093788 | 4/1988 | Japan | 544/71 |
| 63-303983 | 12/1988 | Japan | 544/71 |

Primary Examiner—Joseph L. Schofer
Assistant Examiner—Alex H. Walker
Attorney, Agent, or Firm—Birch, Stewart, Kolasch & Birch

[57] ABSTRACT

A novel photochromic compound and a polymer comprising the photochromic compound are disclosed. The novel photochromic compound of the present invention is a spirooxazine compound having an addition polymerizable organic functional group or a ring-opening polymerizable organic functional group therein.

6 Claims, No Drawings

PHOTOCHROMIC COMPOUND

This application is a continuation of application Ser. No. 07/495,599 filed on Mar. 19, 1990, now abandoned, which is a divisional application of Ser. No. 07/151,601 filed Feb. 2, 1988 now abandoned.

BACKGROUND OF THE INVENTION

I. Field of the Invention

This invention relates to a novel photochromic compound and to a novel photochromic polymer containing the photochromic compound, as well as to a process of producing the polymer and to a use of the polymer.

II. Description of the Prior Art

As the compounds which exhibit photochromism, spiro series compounds are best studied because of their great color change. Among these, spiropyran-based compounds show great color change, so that they are currently used by being dispersed in a solution or in a macromolecular medium, or by being chemically bonded to a carrier. It is known that in cases in which the photochromic compound is polymerized via chemical bonds, the elution of the photochromic compound from the macromolecular medium is reduced and the thermal stability of the photochromic compound is enhanced (G. Smets, "J. Polym. Sci. Polym. Chem. Ed." Vol. 12, pp.2511–2523 (1974)). There are various methods by which the spiropyran-based compounds may be carried on a macromolecular carrier. Among these, the most practical one is the method in which a polymerizable functional group is introduced into the photochromic compound, and then the compound is homopolymerized or copolymerized with a polymerizable compound. The spiropyran compounds having a polymerizable functional group are disclosed in "J. Polym. Sci. Polym. Chem. Ed." Vol. 12, pp.2511–2523 (1974), Japanese Patent Publication (Kokoku) No. 307114/79 and Japanese Patent Disclosure (Kokai) No. 76490/86.

However, the spiropyran-based compounds have a drawback in that their durability against repeated coloring-decoloring cycles is low, which hinders the practical use of the compounds.

As photochromic compounds which show large color change and have great durability against repeated coloring-decoloring cycles, indolinospironaphthooxazine is disclosed in Japanese Patent Publication Nos. 28892/70 and 48631/74, and piperidinospironaphthooxazine is disclosed in Japanese Patent Disclosure (Kokai) No. 145089/87. These spirooxazine compounds are used by being dispersed in a solution or in a macromolecular medium.

The dispersion of the spirooxazine compounds employed in the prior art has the following problems:

(1) The solubility of the spirooxazine compound is limited, so that the amount of the spirooxazine compound which may be added to the macromolecular medium is limited accordingly. Thus, a problem of low color density is brought about.

(2) When the spirooxazine compound-containing macromolecular medium is used as a coating composition, the spirooxazine compound may be precipitated because of the evaporation of the solvent.

(3) If the spirooxazine compound-containing macromolecular medium is subjected to heat, to a chemical or to vacuum, evaporation, extraction or elution of the compound may occur.

(4) The thermal and chemical properties of the spirooxazine compound-containing macromolecular medium is reduced due to the plasticization of the macromolecules.

In view of the ease of handling and chemical resistance, it is preferred that the photochromic compound be made into a polymer by homopolymerizing or copolymerizing the photochromic compound. Usually, such a photochromic polymer is used by being applied on a substrate after being dissolved in a solvent. As the solvent, an organic solvent is usually used. However, if the solution is applied on a plastic substrate, the organic solvent may dissolve the plastic substrate. Further, it is dangerous to use an organic solvent. Therefore, an aqueous solvent is preferred to an organic solvent. In view of this, a technique in which a water-soluble photochromic compound is dispersed in a water-soluble polymer is proposed (Japanese Patent Disclosure (Kokai) No. 23787/73).

However, the durability of such a composition is low. A water-soluble photochromic compound as well as a water-soluble copolymer thereof, which excells in durability, have not yet been obtained.

SUMMARY OF THE INVENTION

Accordingly, the object of the present invention is to provide a photochromic compound which exhibits high color density, which is stable against heat and solvent, and which has a great repeating durability against coloring-decoloring cycles, as well as to provide a photochromic polymer containing such a photochromic compound.

Another object of the present invention is to provide a water-soluble photochromic polymer with the above-mentioned excellent properties, which has a sufficient durability.

Still another object of the present invention is to provide a resin containing a photochromic polymer with the above-mentioned excellent properties, which resin can be used for print processing on a fabric or the like, as well as a process of producing such resin.

The present invention provides a photochromic compound which is a spirooxazine compound having an organic functional group which can participate in addition polymerization (hereinafter referred to as addition polymerizable organic functional group) or an organic functional group which can participate in ring-opening polymerization (hereinafter referred to as a ring-opening polymerizable organic functional group).

The present invention further provides a photochromic polymer comprising the photochromic compound of the present invention which compound is bonded in the polymer via covalent bonds.

The present invention still further provides a photochromic polymer comprising as repeating units the following A and B components: A component: spirooxazine monomer of the present invention; B component: a monomer having a group which can form a hydrogen bond (hereinafter referred to as hydrogen bondable group).

The present invention still further provides a resin having photochromic properties, which comprises photochromic particles dispersed in a resin component which can be formed into a film, which particles have an average particle size of 0.1 μm to 100 μm, the photochromic particles comprising the covalently bonded spirooxazine compound of the present invention.

The present invention still further provides a composition comprising in a solvent a resin component and the photochromic particles mentioned in the preceding paragraph, which composition is able to be coated on a substrate such as cloth by screen print, etc.

The present invention still further provides a process of producing the resin of the present invention comprising the steps of coating on a substrate the composition of the present invention; and drying or curing the coated composition.

By the present invention, a polymerizable photochromic compound which exhibits high color density, which is stable against heat and solvents, and which has a great durability against coloring-decoloring cycles was provided. Since the photochromic compound of the present invention has a polymerizable functional organic functional group, the photochromic compound may readily be polymerized or copolymerized into a polymer. The polymer retains the above-mentioned excellent properties of the photochromic compound of the present invention. In a preferred embodiment, the polymer is in the form of particles which may be suitably dispersed in a resin. The resin may be used in wide variety of applications. According to the present invention, a water-soluble photochromic polymer with the above-mentioned excellent properties is provided. Since this photochromic polymer is water-soluble, an aqueous medium may be used for the solvent of the polymer. Thus, when the polymer solution is applied on a plastic substrate, the solvent does not dissolve the substrate, and there is no problem on the safety of handling of the solvent.

DETAILED DESCRIPTION OF THE PREFERRED EMBODIMENTS

As mentioned above, the photochromic compound of the present invention is a spirooxazine compound having an addition polymerizable organic functional group or a ring-opening polymerizable organic functional group. In view of introducing the compound into acrylic resin which has an excellent weatherability, the preferred addition polymerizable organic functional group is one which can participate in radical polymerization (hereinafter referred to as a radical polymerizable organic functional group). Preferred examples of the radical polymerizable unsaturated organic functional group include acrylic acid ester group, methacrylic acid ester group, acrylic acid amide group, methacrylic acid amide group and vinyl benzoic acid ester group. Preferred ring-opening polymerizable organic functional group includes an epoxy ring-opening polymerizable organic functional group. The position at which the polymerizable organic functional group is to be introduced is not restricted, and the polymerizable group may be introduced as a substituent of, for example, the naphthalene ring, quinoline ring or the benzene ring. Further, the polymerizable group may be introduced in the N-position of the indoline ring. In cases in which the enhancement of the durability of the photochromic compound is especially desired, the polymerizable group may preferably be introduced in the naphthalene ring or in the quinoline ring, and in cases in which the control of the coloring density is desired, the polymerizable group may preferably be introduced in the N-position of the indoline ring. Two or more polymerizable organic functional groups may be introduced in one compound, and the groups may be the same or different.

Preferred examples of the photochromic compound of the present invention will now be described in detail.

The first group of the preferred examples of the photochromic compound of the present invention is represented by the following formula [I]:

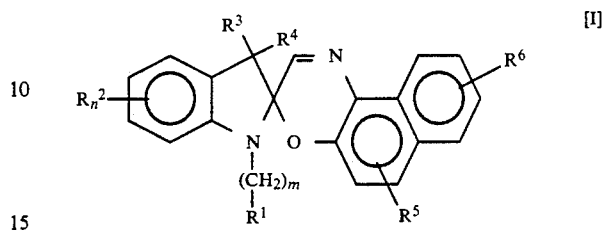

wherein $R^1$ represents an addition polymerizable or a ring-opening polymerizable organic functional group; $R^2$, $R^5$ and $R^6$, the same or different, represent hydroxyl group, amino group, organic substituted amino group, $C_1$–$C_6$ alkoxyl group, $C_1$–$C_{20}$ alkyl group, halogen, carboxyl group, $C_2$–$C_{10}$ group or nitro group; $R^3$ and $R^4$, the same or different, represent $C_1$–$C_{10}$ alkyl group, $C_7$–$C_{12}$ aralkyl group, or $R^3$ and $R^4$ cooperatively represent $C_6$–$C_8$ alicyclic ring with a spiro carbon atom, norbornyl group or adamantyl group; m is an integer of 1–30; and n is an integer of 0–4. When the n is 2–4, the $R^2$ may be the same or different.

Preferred examples of the spirooxazine compound of represented by the formula [I] may include
1-acryloxyethyl-3,3-dimethylspiro[indoline-2,3'-[3H]naphtho[2,1-b](1,4)oxazine],
1-methacryloxyethyl-3,3-dimethylspiro[indoline-2,3'-[3H]naphtho[2,1-b](1,4)oxazine],
1-methacryloxypropyl-3,3-dimethylspiro[indoline-2,3'-[3H]-naphtho[2,1-b](1,4)oxazine],
1-methacrylamideethyl-3,3-dimethyl-5-chlorospiro[indoline-2,3'-[3H]-naphtho[2,1-b](1,4)oxazine],
1-methacryloxyethyl-3,3-dimethyl-8'-methoxyspiro-(p-vinylphenethyl)-3,3-dimethyl-5,6-dichlorospiro[-indoline-2,3'-[3H]-naphtho[2,1-b](1,4)oxazine].

The second group of the preferred examples of the photochromic compound of the present invention may be represented by the following formula [II]:

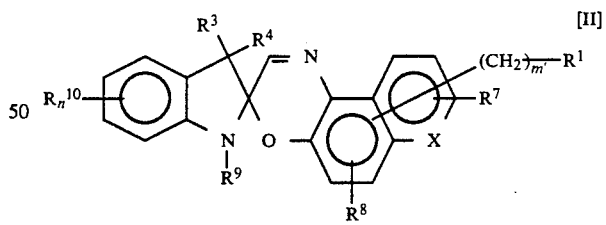

wherein $R^1$ represents the same meaning as in formula [I]; $R^7$, $R^8$ and $R^{10}$, the same or different, represent organic substituted amino group, $C_1$–$C_6$ alkoxy group, $C_1$–$C_{20}$ alkyl group, halogen, carboxyl group, $C_2$–$C_{10}$ acyl group, nitro group or hydrogen; $R^9$ represents $C_1$–$C_{30}$ alkyl group, phenyl group, substituted phenyl group, $C_7$–$C_{12}$ aralkyl group, $C_7$–$C_{12}$ substituted aralkyl group, $C_1$–$C_{30}$ hydroxyalkyl group, $C_1$–$C_{30}$ aminoalkyl group, $C_4$–$C_{30}$ alkyl acrylate group, $C_4$–$C_{30}$ alkylamide acrylate group, $C_5$–$C_{30}$ alkyl methacrylate group or $C_5$–$C_{30}$ alkylamide methacrylate group; $R^3$ and $R^4$ represent the same meaning as $R^3$ and $R^4$ in formula [I]; X represents N or CH; m' represents an integer of 0–10;

and n represents the same meaning as in formula [I]. When the n is 2-4, each $R^{10}$ may be the same or different.

Preferred examples of the spirooxazine compound represented by the formula [II] may include
1,3,3-trimethyl-9'-methacryloxyspiro[indoline-2,3'-[3H]-naphtho[2,1-b](1,4)oxazine],
1,3,3-trimethyl-5'-methacryloxymethylspiro[indoline-2,3'3H]-naphtho[2,1-b](1,4)oxazine],
1,3,3-trimethyl-9'-methacrylamidespiro[indoline-2,3'-3H]-naphtho[2,1-b](1,4)oxazine],
1,3,3-trimethyl-5-chloro-8'-acryloxyspiro[indoline-2,3'-3H]-naphtho[2,1-b](1,4)oxazine],
1-benzyl-3,3-dimethyl-9'-vinylbenzoyloxyspiro[indoline2,3'-[3H]-naphtho[2,1-b](1,4)oxazine] and
3-trimethyl-9'-methacryloxyspiro[indoline-2,3'-[3H]-pyrido[2,1-b](1,4)benzooxazine].

The third group of the preferred examples of the photochromic compound of the present invention may be represented by the following formula [III]:

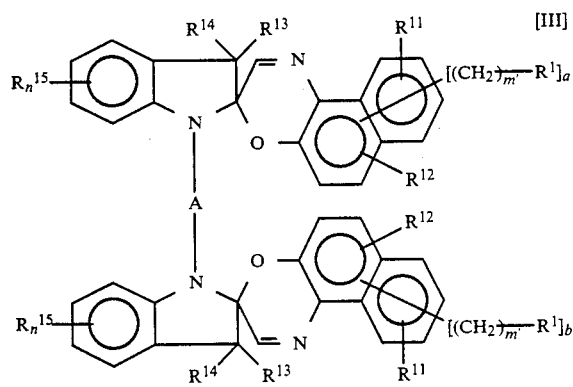

wherein $R^1$ represents the same meaning as in formula [I]; $R^{11}$, $R^{12}$ and $R^{15}$, the same or different, represent organic substituted amino group, $C_1-C_6$ alkoxy group, $C_1-C_{20}$ alkyl group, halogen, carboxyl group, $C_2-C_{10}$ acyl group, hydroxyl group, nitro group, $C_1-C_{10}$ hydroxyalkyl group or hydrogen; $R^{13}$ and $R^{14}$, the same or different, represent $C_1-C_{10}$ alkyl group, aryl group, $C_7-C_{12}$ aralkyl group, or $R^{13}$ and $R^{14}$ cooperatively represent $C_6-C_8$ alicyclic ring with a spiro carbon atom, norbornyl group or adamantyl group; A represents $C_1-C_{30}$ alkylene group, $C_1-C_{30}$ alkylene(poly)oxyalkylene group, or $C_8-C_{20}$ alkylenearylalkylene group; a and b, the same or different, are 0 or 1 and (a+b) is 1 or 2; m' and n represent the same meaning as in formula [II], respectively. When n is 2-4, each $R^{15}$ may be the same or different. Further, each $R^{11}$, $R^{12}$, $R^{13}$ and $R^{14}$ may be the same or different, respectively.

Preferred examples of the spirooxazine compound represented by the formula [III] may include
1,1''-(1,5-pentanediyl)bis[3,3-dimethyl-9'-methacryloxyspiro[indoline-2,3'-[3H]-naphtho[2,1-b](1,4)oxazine]],
1,1''-[1,4-phenylenebis(methylene)]bis[3,3-dimethyl-5'-(meta)acryloxymethylspiro[indoline-2,3'-[3H]-naphtho[2,1-b](1,4)oxazine]],
1,1''-(1,4-butanediyl)bis[5,6-dichloro-3,3-dimethyl-8'-(meta)acryloxyspiro[indoline-2,3'-[3H]-naphtho[2,1-b](1,4)oxazine]].

The fourth group of the preferred examples of the photochromic compound of the present invention may be represented by the following formula [IV]:

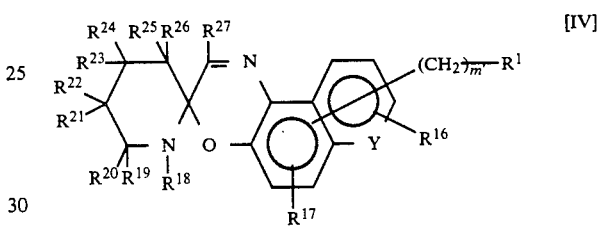

wherein $R^{16}$ and $R^{17}$, the same or different, represent organic amino group, $C_1-C_6$ alkoxyl group, $C_1-C_{20}$ alkyl group, halogen, carboxyl group, $C_2-C_{10}$ acyl group, cyano group, nitro group or hydrogen; $R^{18}-R^{27}$ represent, the same or different, $C_1-C_{30}$ alkyl group, phenyl group, substituted phenyl group, $C_7-C_{12}$ aralkyl group, $C_7-C_{12}$ substituted aralkyl group, $C_1-C_6$ alkoxyl group, carboxyl group, nitro group or hydrogen; Y represents N or C—$R^{16}$ (wherein $R^{16}$ represents the same meaning as mentioned above); and m' represents the same meaning as in formula [II].

The preferred examples of the spirooxazine compound represented by the formula [IV] may include the compounds represented by the following formula [V] to [IX].

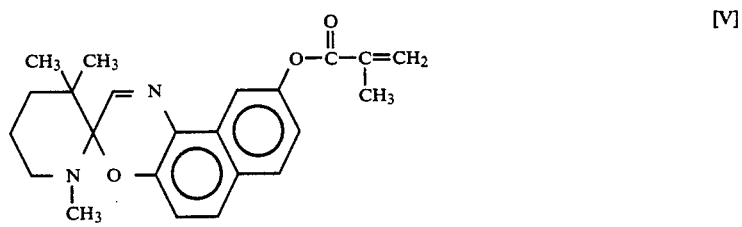

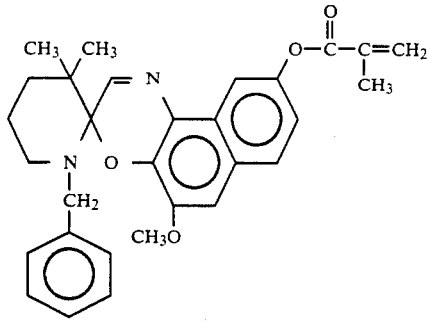

[VI]

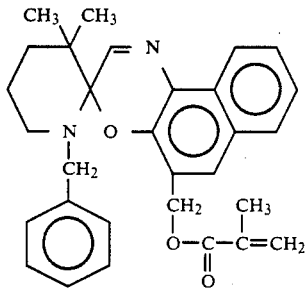

[VII]

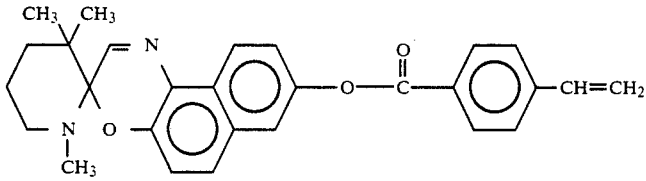

[VIII]

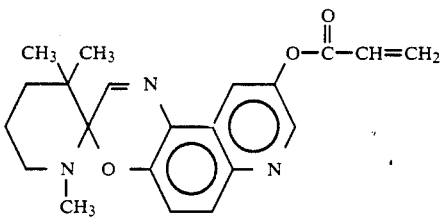

[IX]

The above-described spirooxazine compounds of the present invention may be not only homopolymerized but also copolymerized with other copolmerizable compounds so as to readily form a photochromic polymer. Thus, although the spirooxazine compounds of the present invention are photochromic compounds which absorb visible light upon irradiation of ultraviolet light in solution or in a polymer dispersion, the spirooxazine compounds may also be used for forming useful photochromic polymers by being homopolymerized or copolymerized with other copolymerizable compounds via covalent bonds. Preferred compounds used for copolymerization of the spirooxazine compounds of the present invention may include monofunctional polymerizable compounds such as alkyl acrylate, alkyl methacrylate, hydroxyalkyl (meth)acrylate, styrene, (meth)acrylic acid, substituted styrene derivative, N-substituted maleimide, maleic anhydride, (meth)acrylonitrile, (meth)acrylic acid amide, vinylpyrrolidone, methylvinyl ketone, vinyl acetate and vinylidene chloride; and polyfunctional polymerizable compounds such as divinylbenzene, ethyleneglycoldi(meth)acrylate, isopropanedioldi(meth)acrylate, and di-, tri- or tetra-(meth)acrylate of trimethylolpropane and pentaerythritol. By appropriately selecting the copolymerizable compound, the stability of the colored polymer may be freely controlled to a considerable extent. Copolymerization with a monomer having a hydrogen bondable group is effective for the promotion of the thermal stability of the colored copolymer.

Further, by selecting a copolymerizable compound which confers water-solubility to the copolymer, such as, for example, hydroxyethyl methacrylate, (meth)acrylic acid, (meth)acrylamide or the like, it is possible to make the copolymer water-soluble. The monomer conferring water-solubility may be any monomer of which the homopolymer or copolymer is water soluble, or a polymer derived therefrom shows water-solubility after modification such as saponification. In view of the compatibility with the photochromic compound, the preferred examples of the copolymerizable compound which gives water-solubility to the copolymer may include N-vinyl-2-pyrrolidone, vinyl acetate, acrylamide, methacrylamide, N,N-dimethylacrylamide, N,N-dimethyl methacrylamide, other substituted (meth)acrylamide, N,N-dimethylaminoethyl acrylate, N,N-dimethylaminoethylmethacrylate, acrylic acid and methacrylic acid.

Further, for imparting other properties to the copolymer, a third monomer may be copolymerized as long as the resulting copolymer shows water-solubility. A preferred example of the third monomer is one which may be post-cross-linkable because the copolymer may be cured after being coated on a substrate. The content of the water-solubility-conferring monomer is preferably 50 mol % to 99.9 mol %. The content of the photochromic compound of the present invention may preferably be 0.1 mol % to 50 mol %. If the content of the photochromic compound is less than 0.1 mol %, the photochromism of the copolymer may be insufficient and if it is more than 50 mol %, the water-solubility may be reduced. It should be noted that the term "water-soluble" means that the solubility of the polymer in water is 1 g/l or more at 20° C.

In a preferred mode of the present invention, the polymer containing the photochromic compound of the present invention is in the form of particles. The above-mentioned polymer containing the photochromic compound of the present invention may be formed into particles. Further, a mixture of the polymer containing the photochromic compound of the present invention and other polymers may be formed into particles.

Since the above-mentioned photochromic particle of the present invention contains the photochromic compound via covalent bonds, the elution of the photochromic compound out of the particle is prevented, so that the durability of the polymer is high. The content of the photochromic compound of the present invention in the polymer particle may preferably be 0.1% by weight to 50% by weight, although the preferred content varies depending upon the desired properties of the particles.

The polymer particle should have an average particle size of 0.1 $\mu$m to 100 $\mu$m. The average particle size herein means the average of the particle size of each particle, and the particle size is represented by the diameter of the particle in cases in which the particle is spherical, or by the average of the length of the longer axis and shorter axis of the particle in cases in which the particle is in the form of scale, cube or parallelpiped. If the average particle size is less than 0.1 $\mu$m, it is difficult to obtain such particles and in cases in which the particles are contained in a cosmetic, the cosmetic may have a problem with respect to its safety. On the other hand, if the average particle size is more than 100 $\mu$m, the efficiency of the photochromic reaction is reduced, so that the color density in the colored state may be lowered. Although the maximum particle size of the particles is not limited, since the purpose of forming the polymer into a particle is to enhance the photochromic property and to maintain the high quality, it is preferred that the maximum particle size be not more than 500 $\mu$m.

The polymer particles with this range of average particle size may be produced by conventional methods. As a method utilizing physical force, there is a method in which the polymer containing the photochromic compound is made into particles by mechanically pulverizing the polymer or by spray-drying the polymer. Methods utilizing a chemical process include a method in which the monomer is polymerized (Shinzo Omi, "Powder and Industry" Vol. 24, p.11 (1986)), and chemical pulverizing methods (Japanese Patent Disclosure (Kokai) Nos. 6652/75, 219236/83, 197734/85, and Japanese Patent Publication (Kokoku) Nos. 51566/84, 17851/86 and 28688/86). The method in which the monomer is polymerized includes a method in which the photochromic compound of the invention is mixed with another monomer and then the mixture is subjected to emulsion polymerization, soap-free emulsion polymerization, non-aqueous dispersion polymerization, seed emulsion polymerization or suspension polymerization. The chemical pulverizing method includes a method in which the polymer containing the photochromic compound is dissolved in a solvent at high temperature and then the solution is cooled to precipitate the polymer; a method in which the polymer is dissolved in a solvent and then a poor solvent of the polymer, which is miscible with the solvent, is added to the solution to precipitate the polymer particles; and a method in which a polymer solution containing the polymer in an organic solvent is mixed with a poor solvent of the polymer, which is immiscible with the organic solvent, and the organic solvent is removed by heating or evaporation to obtain a dispersion of the polymer particles, and then the polymer particles are recovered. These methods are appropriately selected depending on the desired particle size and the characteristics of the photochromic compound.

In view of promoting the durability and color density of the polymer particles, it is preferable to incorporate an antioxidant or a sensitizer in the particles. It is also possible to promote the prevention of blocking and to promote the fluidity by adsorbing or sprinkling superfine powder of silica or alumina on the polymer particles in dispersed and/or dried form.

The polymer particles containing the photochromic compound of the present invention have various uses. Since the polymer is in the form of particles, the photochromic reaction may be conducted efficiently and the color density in the colored state is high. In general, since the photochromic compounds change the color thereof by absorbing ultraviolet light, the efficiency of absorbing ultraviolet light of the particles is high. Therefore, if the polymer particles are contained in a cosmetic, the human skin may be effectively protected from ultraviolet light, and the cosmetic shows color change to present a fashionable appearance. Since the efficiency of the photochromic reaction is high, the particles may also be applied in various paints, additives, coating agents and toys.

As an especially useful application of the polymer particles, the particles may be incorporated in a dispersed state in a resin component which can be formed into a film, to present a resin which may be used for printing a substrate such as a fabric. Although the resin component which can be formed into a film may be an organic resin or an inorganic resin, an organic resin is preferred in view of the ease of mixing with the particles. Preferred examples of the organic resin component may include water-soluble polyesters, water-soluble olefin rubbers, polyvinyl alcohols, polyacrylamides, cellulose derivatives, polyethylene glycols, water-soluble acrylic resins, polyurethane resins, polyacrylic acids, polyamide resins, vinyl resins, styrene resins, acrylic resins, polyester resins and epoxy resins Silicone resins may also be used. Among these, in view of the good dispersion state and handling ease in the process, water-soluble polymers and water-dispersible polymers are especially preferred. The resin components may be used independently or in combination.

For the promotion of the physical properties of the film formed from the resin, it is also preferred to post-cross-link (cure) the film.

The content of the polymer particles in the resin may be 0.01–99.9% by weight, and the content may be appropriately selected depending on the desired characteristics of the resin.

It is also possible to incorporate in the resin a pigment, weather stabilizer, various reaction initiator, surface active agent and the like.

The resin may be produced by coating on a substrate a composition containing the photochromic polymer particles and the resin component in a solvent, and then drying or curing the coated composition. Any solvent which dissolves the resin component and which does not completely dissolve the particles may be used in the production of the resin. If the polymer constituting the particles is a thermoplastic resin, a poor solvent such as water and alcohol may preferably be employed, and if the polymer is a thermosetting polymer, in addition to the poor solvents, various organic solvents may be used. The mixing ratio of the resin component and the solvent may be 1:999 to 999:1 by weight and the mixing ratio of (particles + resin component):solvent may be 1:999 to 999:1 by weight, and these may be appropriately selected depending on the desired characteristics of the resin. A plurality of resin components or solvents may be used in combination. It is preferred that the particles be uniformly dispersed in the resin component and in the solvent. A reactive dispersion medium may also be employed as the dispersion medium.

The resin of the present invention may be used for covering any substrate including fabrics, papers, plastic materials, metallic materials and inorganic materials (such as glass and ceramics).

Since the resin having photochromic properties contains the photochromic compound of the present invention included in the particles, the resin has a high light-absorbing efficiency and is colored to a high color density. The photochromic property of the particles may be well controlled by selecting the characteristics of the polymer constituting the particles, so that the resin may be applied in various applications requiring various characteristics. Thus, the resin has various applications. For example, the resin may be printed on a fabric to produce a so called "chameleon" fabric. In this case, the fabric is excellent in durability, that is, the fabric is resistant against washing and dry-cleaning. In other words, the elution of the photochromic compound is prevented when the fabric is subjected to washing or dry-cleaning.

The papers, plastic materials, metallic materials, glass materials coated with the resin may be used in various applications including light-adjusting materials, recording materials, materials for producing fashionable clothes, and sensors.

Another important use of the photochromic compound of the present invention is the application to contact lenses. That is, the photochromic compound of the present invention may be contained as a constituent of the contact lens via covalent bonds. It is advantageous to incorporate the photochromic compound in the contact lens because the hydrophilic ion-cleaved compound generated in the colored state gives hydrophilicity (wetting property) to the surface of the contact lens and the compatibility with the cornea is promoted.

Any organic polymer which is conventionally used in the contact lens may be used as the major component of the contact lens of the present invention. Examples of the materials used as the major constituent of the contact lens may include poly(meth)acrylic acid esters such as polymethyl(meth)acrylate; polymers of unsaturated aromatic compounds such as styrene; polyhydroxyalkyl(meth)acrylates; polyvinyllactams; substituted celluloses such as cellulose acetate butylate; polymers containing silicon; and copolymers thereof. To confer mechanical strength, an appropriate cross-linking agent such as polyfunctional(meth)acrylate and divinylbenzene may preferably be added. Further, for the purpose of promoting the compatibility with the cornea, a hydrophilic component such as unsaturated resin acid may be copolymerized to promote the hydrophilicity, and silicon compounds may be copolymerized to promote the oxygen permeability as in the prior art.

The incorporation of the photochromic compound of the present invention in the contact lens may be accomplished by copolymerizing the spirooxazine compound with the material of the contact lens via covalent bonds. This method is especially preferred in view of the prevention of the elution of the photochromic compound and durability of the obtained contact lens.

The method of producing the contact lens differs depending on whether the contact lens to be produced is a soft contact lens or a hard contact lens. The hard contact lens is usually produced by polishing a button-like polymer obtained by cast polymerization of a mixture of an acrylic monomer such as alkyl(meth)acrylate and (meth)acrylic acid, a bifunctional or polyfunctional cross-linking agent and a polymerization initiator. The contact lens with photochromic property may be produced in the similar manner. That is, the contact lens with photochromic property may be obtained by polymerizing the above-mentioned mixture which further contains the photochromic compound of the present invention.

The soft contact lens is usually produced by pouring a mixture of an acrylic monomer such as alkyl(meth)acrylate, (meth)acrylic acid and hydroxyalkyl(meth)acrylate, a cross-linking agent and a polymerization initiator in a mold and by conducting cast polymerization. The soft contact lens with the photochromic property may be produced in a similar manner. That is, the contact lens with the photochromic property may be obtained by polymerizing the above-mentioned mixture which further contains the photochromic compound of the present invention.

The content of the photochromic compound in the contact lens may be appropriately selected depending on the desired color density, but usually 0.1–40% by weight in view of the color density and physical properties of the lens.

It is also preferred to incorporate additives such as a sensitizer and an antioxidant, for the purpose of promoting the color density and durability.

The photochromic contact lens of the present invention has light-adjusting property, anti-glare property and is fashionable. Further, the contact lens has an advantage easily distinguished whether a person is wearing the contact lens or not. Thus, the contact lens has excellent functions and high added values, and so it is useful.

The spirooxazine compound of the present invention may be produced by various processes. Among these processes, the most common process which gives high yield is to react a methylene indoline derivative represented by one of the following formulae [X] to [XIII] with a nitrosonaphthol derivative of the following formula [XIV] or [XV] in a conventional manner and then purify the reaction mixture by column chromatography or recrystallization.

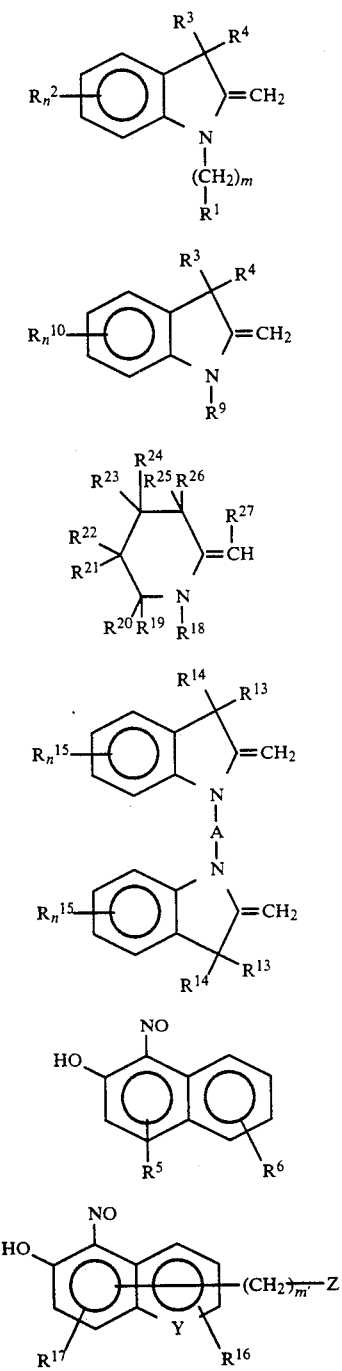

In the above formulae, each symbol has the same meaning as in the formulae [I] to [IV]. Z represents hydroxyl group, amino group or a polymerizable organic functional group. In cases in which Z is hydroxyl group or amino group, the introduction of the polymerizable organic functional group may be effected by reacting the spirooxazine compound obtained by the above reaction, which has a hydroxyl group or an amino group, with (meth)acrylic acid chloride, (meth)acrylic acid, or vinyl benzoic acid to form ester or amide between the hydroxyl group or the amino group and the latter reactant. Alternatively, the polymerizable organic functional group may be preliminarily introduced into the nitrosonaphthol derivative or nitrosohydroxylquinoline derivative, and thereafter the spirooxazine compound may be produced in accordance with the above-mentioned reaction.

Incorporation of the photochromic compound of the present invention in a polymer may be conducted by, as mentioned above, homopolymerizing the compound or copolymerizing the compound with another monomer. Further, the photochromic compound of the present invention may be bonded via covalent bonds to a polymer having a copolymerizable property.

Two or more photochromic compounds of the present invention may be employed in combination to present mixed coloring. It is also possible to use the photochromic compounds of the present invention in combination with another photochromic compound to present mixed coloring.

The photochromic compound of the present invention as well as the polymers (including copolymers) thereof have various uses. When used as a lens or a toy, the photochromic polymer in the form of a molded body or a covering film may be employed. When employed in automobile glass articles such as front glass, side glass and sunroofs, the photochromic polymer may be laminated on the glass. Further, the photochromic compound of the present invention may be used in cosmetics and ornamental articles. Further, the photochromic polymer may be formed into fibers and a fabric may be obtained from the fibers to produce a practical "chameleon" fabric. The fabric may be subjected to dry-cleaning because of the great chemical resistance.

EXAMPLES

The present invention will now be described in more detail by way of examples. The examples are presented for the illustration purposes only and should not be interpreted in any restrictive way.

EXAMPLE 1

In 100 ml of ethanol, 9.2 g (53 mmol) of 1,3,3-trimethyl-2-methyleneindoline and 10 g (53 mmol) of 1-nitroso-2,7-dihydroxynaphthalene were dissolved and the solution was heated to reflux for 3 hours. After removing the solvent, recrystallization was conducted using benzene to obtain 4 5 g of 1,3,3-trimethyl-9'-hydroxyspiro[indoline-2,3'-[3H]naphtho[2,1-b](1,4)oxazine] in the form of green-white solid. In 50 ml of methylene dichloride, 1.5 g (4.4 mmol) of the thus obtained spirooxazine compound was dissolved and 0.6 g (6 mmol) of the methacrylic acid chloride was added dropwise at room temperature and the mixture was allowed to react. After removal of the solvent, purification by column chromatography and recrystallization from methanol was conducted to obtain 1.2 g of 1,3,3-trimethyl-9'-methacryloxyspiro[indoline-2,3'-[3H]-naphtho[2,1-b](1,4)oxazine] as white solid

|  | C | H | N |
|---|---|---|---|
| Calcd (%) | 75.7 | 5.8 | 6.8 |
| Found (%) | 75.3 | 5.6 | 6.4 |

IR spectrum:
1730 (cm$^{-1}$) (C=O (ester) stretching vibration)
1460–1480 (cm$^{-1}$) (C=N— (oxazine ring) stretching vibration)
1080 (cm$^{-1}$) (C—O (oxazine ring) stretching vibration)

EXAMPLE 2

In 100 ml of ethanol, 7.0 g (40 mmol) of 1,3,3-trimethyl-2-methyleneindoline and 8.0 g (40 mmol) of 3-hydroxymethyl-1-nitroso-2-naphthol were dissolved and the solution was heated to reflux for 3 hours. After removal of the solvent, purification was conducted by column chromatography and recrystallization from hexane to obtain 3.0 g of 1,3,3-trimethyl-5'-hydroxymethylspiro [indoline-2,3'-[3H]-naphtho[2,1-b](1,4)oxazine] as a white solid. In 50 ml of methylene dichloride, 1.1 g (3 mmol) of the thus obtained spirooxazine compound was dissolved and 4 ml of triethylamine was added thereto, and then 0.5 g (5 mmol) of methacrylic acid chloride was added dropwise thereto at room temperature and the mixture was allowed to react. After removal of solvent, purification was conducted by column chromatography and recrystallization from hexane to obtain 1.0 g of 1,3,3-trimethyl-5'-methacryloxymethylspiro[indoline-2,3'-[3H]-naphtho[2,1-b](1,4)oxazine] as a light yellow solid.

|           | C    | H   | N   |
|-----------|------|-----|-----|
| Calcd (%) | 76.1 | 6.1 | 6.6 |
| Found (%) | 76.1 | 6.2 | 6.5 |

IR spectrum:
1720 (cm$^{-1}$) (C=O (ester) stretching vibration)
1460–1480 (cm$^{-1}$) (C=N— (oxazine ring) stretching vibration)
1100 (cm$^{-1}$) (C=O (oxazine ring) stretching vibration)

EXAMPLE 3

The 1,3,3-trimethyl-9'-methacryloxyspiro[indoline-2,3'-[3H]-naphtho[2,1-b](1,4)oxazine] obtained in Example 1 was dissolved in acetone. To the resulting colorless solution, ultraviolet light was irradiated. Upon irradiation, the solution was colored in blue ($\lambda_{max}$=605 nm). Upon stopping the irradiation, the color instantly disappeared and the solution was returned to a colorless state. Coloring-decoloring cycle was able to be repeated many times.

EXAMPLE 4

By a typical conventional radical polymerization method, 0.2 g of the spirooxazine compound obtained in Example 1 and 2.8 g of methyl methacrylate were polymerized. Purification by reprecipitation from methanol was repeated to obtain a copolymer. The copolymer was dissolved in a solvent and the solution was applied on a slide glass. The film obtained by drying the coated solution was irradiated with ultraviolet light. As a result, the film was colored in blue ($\lambda_{max}$=604 nm). By this, it was confirmed that the photochromic compound is carried in the polymer. The coloring-decoloring cycle was able to be repeated many times.

EXAMPLE 5

By a typical conventional radical polymerization method, 0.2 g of the spirooxazine compound obtained in Example 2 and 2.8 g of styrene were polymerized. Purification by reprecipitation from methanol was repeated to obtain a copolymer. The copolymer was dissolved in a solvent and the solution was applied on a slide glass. The film obtained by drying the coated solution was irradiated with ultraviolet light. As a result, the film was colored in blue ($\lambda_{max}$=615 nm). By this, it was confirmed that the photochromic compound is carried in the polymer. The coloring-decoloring cycle was able to be repeated many times.

EXAMPLE 6

The films obtained in Examples 4 and 5 were immersed in methanol or hexane for 24 hours. Thereafter, ultraviolet light was irradiated to the films. No difference was observed between the color density before and after the immersion. By this, it was proved that the elution of the photochromic compound from the polymer did not occur and so the polymer has a great durability.

EXAMPLE 7

In 150 ml ethanol, 16 g (0.06 mol) of 1-methacryloxyethyl-3,3-dimethyl-2-methyleneindoline and 10.4 g (0.06 mol) of 1-nitroso-2-naphthol were dissolved and the solution was heated to reflux for 5 hours. After removal of the solvent, the residue was purified by column chromatography to obtain 2.6 g (yield 10.3%) of 1-methacryloxyethyl-3,3-dimethylspiro[indoline-2,3'-[3H]-naphtho[2,1-b](1,4)oxazine] was obtained as a yellow-white solid.

|           | C    | H   | N   |
|-----------|------|-----|-----|
| Calcd (%) | 76.1 | 6.1 | 6.6 |
| Found (%) | 76.2 | 6.5 | 6.5 |

IR spectrum:
1720 (cm$^{-1}$) (C=O (ester) stretching vibration)
1460–1480 (cm$^{-1}$) (C=N— (oxazine ring) stretching vibration)
1080 (cm$^{-1}$) (C—O (oxazine ring) stretching vibration)

EXAMPLE 8

The spirooxazine compound obtained in Example 7 was dissolved in acetone to obtain a colorless solution. Upon irradiation of the solution with ultraviolet light at a low temperature (10° C.), the solution was colored in blue. The coloring-decoloring cycle was able to be repeated many times.

EXAMPLE 9

The spirooxazine compound obtained in Example 7 was dissolved in methylene dichloride solution of polymethyl methacrylate and the solution was applied on a slide glass and dried. The thus prepared film was subjected to ultraviolet light at room temperature. Upon irradiation, the film was colored in blue. The coloring-decoloring cycle was able to be repeated many times.

EXAMPLE 10

One equivalent of the spirooxazine compound obtained in Example 7 and 19 equivalents of methyl methacrylate were polymerized by a typical conventional radical polymerization method. After purifying by reprecipitation method, a copolymer was obtained. The copolymer was dissolved in a solvent and the solution was applied on a slide glass and dried to obtain a transparent film. Upon irradiation of the film with ultraviolet light, the film was colored in blue. By this, it was confirmed that the photochromic compound was carried. Further, the coloring-decoloring cycle was able to be repeated many times.

EXAMPLE 11

One equivalent of 1-methacryloxyethyl-3,3-dimethyl8'-methoxyspiro[indoline-2,3'-[3H]-naphtho[2,1-b](1,4)oxazine] obtained by the similar manner as in Example 7 was polymerized with 19 equivalents of styrene in the same manner as in Example 10 to obtain a copolymer. Upon irradiation with ultraviolet light, the colorless copolymer was colored in blue. The coloring-decoloring cycle was able to be repeated many times.

EXAMPLE 12

One equivalent of 1-methacryloxyethyl-3,3-dimethyl-5-chlorospiro[indoline-2,3'-[3H]-naphtho[2,1-b](1,4)-oxazine] obtained in the similar manner as in Example 7 was polymerized with 19 equivalents of methyl methacrylate as in Example 10, and a film was prepared from the resulting copolymer as in Example 10. The film, upon irradiation with ultraviolet light, was colored in blue. The coloring-decoloring cycle was able to be repeated many times.

EXAMPLE 13

The film obtained in Example 10 was immersed in methanol for 24 hours. Thereafter, ultraviolet light was irradiated to the films. No difference was observed between the color density before and after the immersion. By this, it was proved that the elution of the photochromic compound from the polymer did not occur and so the polymer has a great durability.

EXAMPLE 14

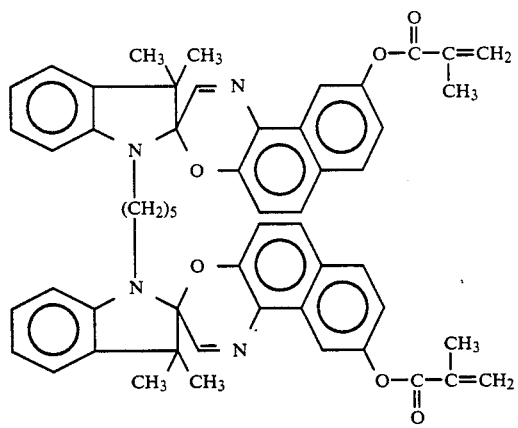

Production of
1,1''-(1,5-pentandiyl)bis[3,3-dimethyl-9'-methacryloxyspiro[indoline-2,3'-[3H]-naphtho[2,1-b](1,4)-oxazine]]

In 200 ml of ethanol, 15.9 g (0.1 mol) of 2,3,3-trimethylindolenine and 10.3 g (0.045 mol) of 1,5-dibromopentane were dissolved, and the solution was heated to reflux for 3 hours to obtain 20 g of dimer of indolenium salt. In 200 ml of ethanol, 11 g (20 mmol) of the thus obtained dimer of indolenium salt, 8.4 g (44 mmol) of 1-nitroso-2,7-dihydroxynaphthalene and 5 ml of ethanol were dissolved and the solution was heated to reflux for 20 hours. After completing the reaction, the solvent was removed and recrystallization from hexane or benzene was conducted to obtain about 3.0 g of spirohydroxynaphthooxazine dimer. In 100 ml of methylene dichloride, 1.0 g (1.3 mmol) of the thus obtained spirohydroxynaphthooxazine dimer was dissolved, and 2 ml of triethylamine was added thereto. Thereafter, 0.31 g (3.0 mmol) of methacrylic acid chloride was added dropwise to the mixture at room temperature and the resulting mixture was allowed to react. After completion of reaction, purification was conducted by column chromatography and by recrystallization from methanol to obtain about 1.0 g of the desired product as a white solid.

|  | C | H | N |
|---|---|---|---|
| Calcd (%) | 76.4 | 6.0 | 6.5 |
| Found (%) | 76.2 | 5.8 | 6.6 |

IR spectrum:
1730 (cm$^{-1}$) (C=O (ester) stretching vibration)
1460–1480 (cm$^{-1}$) (C=N— (oxazine ring) stretching vibration)

EXAMPLE 15

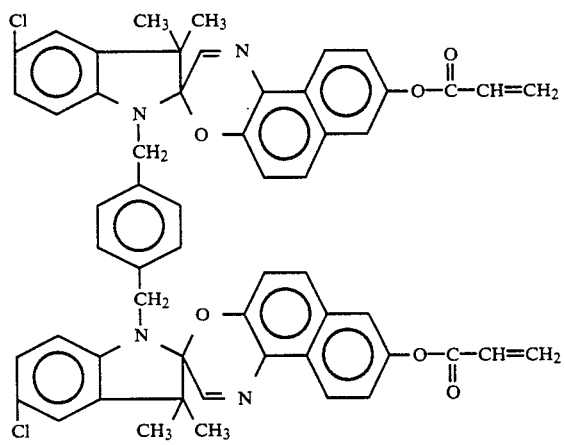

Production of
1,1'''-[1,4-phenylene-bis(methylene)]bis[5-chloro-3,3-dimethyl-8'-acryloxyspiro[indoine-2,3'-[3H]naphtho[2,1-b](1,4)oxazine]]

In 200 ml of methylethyl ketone, 19.4 (0.1 mol) of 5-chloro-2,3,3-trimethylindolenine and 12.0 g (45 mmol) of α, α'-dibromo-p-xylene were dissolved and the solution was heated to reflux for 3 hours to obtain dimer indoleium salt. In 100 ml of ethanol, 6 5 g (10 mmol) of the thus obtained dimer indolenium salt, 3.8 g (20 mmol) of 1-nitroso-2,6-dihydroxynaphthalene and 5 ml of triethylamine were dissolved and the solution was heated to reflux for 20 hours. After completion of the reaction, the solvent was removed and recrystallization was conducted from hexane and benzene to obtain spirohydroxynaphthooxazine dimer. In 50 ml of methylene chloride, 1.0 g (1.2 mmol) of the thus obtained spirohydroxynaphthooxazine dimer was dissolved and 2 ml of triethylamine was added thereto. Thereafter, 0.27 g (3 mmol) of the acrylic acid chloride was added dropwise to the solution at room temperature and the resulting mixture was allowed to react. After completion of the reaction, purification was conducted by column chromatography and recrystallization from methanol to obtain 0.4 g of the desired product as a white solid.

EXAMPLE 16

The spirooxazine dimer obtained in Example 14 was dissolved in chloroform to obtain a colorless solution. Upon irradiation with ultraviolet light, the solution was colored in blue. Upon stopping the irradiation with ultraviolet, the color instantly disappeared. The coloring-decoloring cycle was able to be repeated many times.

EXAMPLE 17

By a typical conventional radical polymerization method, 0.3 g of the spirooxazine dimer obtained in Example 14 was polymerized with 2.0 g of methyl methacrylate in a solvent containing a polymerization initiator to obtain a polymer gel. After extensively washing the polymer gel with a solvent, the gel was irradiated with ultraviolet light. Upon irradiation with ultraviolet light, the gel was colored in blue. By this, it was proved the spirooxazine dimer of the present invention existed in the polymer as a cross-linking component.

EXAMPLE 18

Production of 1,3,3-trimethyl-9'-methacryloxypiperidinospironaphthooxaxine

In 150 ml of ethanol, 6.0 g of 1,3,3-trimethyl-2-methylenepiperidine and 8.1 g of 1-nitroso-2,7-dihydroxynaphthalene were dissolved and the solution was heated to reflux for 5 hours. After removal of solvent, recrystallization was conducted from benzene to obtain 4.0 g of 1,3,3-trimethyl-9'-hydroxypiperidinospironaphthooxazine. This was reacted with methacrylic acid chloride in the presence of triethylamine to introduce methacrylic group into the spirooxazine compound. After purification by column chromatography and recrystallization, 3.5 g of the desired product was obtained as a yellow-white solid.

|  | C | H | N |
|---|---|---|---|
| Calcd (%) | 73.6 | 6.1 | 7.5 |
| Found (%) | 73.5 | 6.2 | 7.5 |

IR spectrum:
1730 (cm$^{-1}$) (C=O (ester) stretching vibration)
1620 (cm$^{-1}$) (C=N— (oxazine ring) stretching vibration)

EXAMPLE 19

Production of 1-benzyl-3,3-dimethyl-5'-methacryloxymethyl-piperidinospironaphthooxazine In 150 ml of ethanol, 5.0 g of 1-benzyl-3,3-dimethyl-2-methylenepiperidine and 7.0 g of 1-nitroso-3-hydroxymethyl-2-naphthol were dissolved and the solution was heated to reflux for 5 hours. After removal of the solvent, recrystallization was conducted from petroleum ether to obtain 3.0 g of 1-benzyl-3,3-diemthyl-5'-hydroxymethylpiperidinospironaphthooxazine. To this, methacrylate group was introduced as in Example 18 and the resulting product was purified as in Example 18 to obtain 2.5 g of the desired product as a white solid.

|  | C | H | N |
|---|---|---|---|
| Calcd (%) | 77.4 | 6.2 | 6.0 |
| Found (%) | 77.3 | 6.1 | 6.1 |

IR spectrum:
1720 (cm$^{-1}$) (C=O (ester) stretching vibration)
1610 (cm$^{-1}$) (C=N— (oxazine ring) stretching vibration)

EXAMPLE 20

By a typical conventional radical polymerization method, 1.0 g of 1,3,3-trimethyl-9'-methacryloxypiperidinospironaphthooxazine and 9.0 g of methyl methacrylate were polymerized. After reprecipitation, 8.0 g of polymer was obtained. This polymer was dissolved in toluene and the solution was applied on a slide glass and dried to obtain a film. Upon irradiation with ultraviolet light, the film was colored in purple. The coloring-decoloring cycle was able to be repeated many times.

EXAMPLE 21

As in Example 20, 1.0 g of 1-benzyl-3,3-dimethyl-5'-methacryloxymethylpiperidinospironaphthooxazine and 9.0 g of styrene were polymerized and a film was prepared from the resulting copolymer. Upon irradiation with ultraviolet light, the film was colored in purple. The coloring-decoloring cycle was able to be repeated many times.

EXAMPLE 22

The films obtained in Example 20 and 21 were immersed in methanol or hexane for 24 hours. Thereafter, ultraviolet light was irradiated to the films. No difference was observed between the color density before and after the immersion. By this, it was proved that the elution of the photochromic compound from the polymer did not occur and so the polymer has a great durability.

EXAMPLE 23

Using an azo series polymerization initiator, 2.3 g of acrylamide and 0.2 g of 1,3,3-trimethyl-9'-methacryloxyindolinospironaphthooxazine were polymerized in ethanol in a sealed vacuum tube to obtain about 2.0 g of polymer after reprecipitation from methanol. The polymer was completely dissolved in water to give a transparent colorless aqueous solution. Upon irradiation with ultraviolet light, this solution was colored in deep blue to show photochromism.

EXAMPLE 24

Using an azo series polymerization initiator, 2.3 g of acrylamide and 0.2 g of 1,3,3-trimethyl-5'-methacryloxyindolinospironaphthooxazine were polymerized in methanol to obtain a polymer. The polymer was completely dissolved in water to give a transparent colorless aqueous solution. Upon irradiation with ultraviolet light, this solution was colored in deep blue to show photochromism.

EXAMPLE 25

Using an azo series polymerization initiator, 4.0 g of N-vinyl-2-pyrrolidone and 0.2 g of 1,3,3-trimethyl-9'-acryloxyindolinospironaphthooxazine were polymerized in dimethylformamide to obtain a polymer. The polymer was completely dissolved in water to give a transparent colorless aqueous solution. Upon irradiation with ultraviolet light, this solution was colored in deep blue to show photocrhomism.

EXAMPLE 26

An aqueous solution of the photochromic polymer obtained in Example 23 which further contains a surface active agent was applied on a polymethyl methacrylate substrate, and the solution was dried to form a polymer film. During this operation, the substrate was not dissolved and a transparent film was formed.

EXAMPLE 27

The weatherability of the film prepared in Example 26 was tested by the exposure of a fade o-meter. The film showed excellent coloring property for as long as 40 hours. Thus, it was proved that the water-soluble photochromic polymer of the present invention is excellent in light resistance.

COMPARATIVE EXAMPLE 1

A conventional water-soluble photochromic compound of the formula below was dispersed in polyvinylpyrrolidone and a film was prepared therefrom. The light resistance of the film was tested as in Example 27. The coloring of the film was stopped after 20 hours of exposure. Thus, it was confirmed that the conventional water-soluble photochromic compound was inferior to the water-soluble photochromic polymer of the present invention in light resistance.

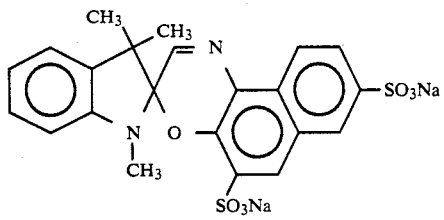

EXAMPLE 28

To 450 parts by weight of ethanol in which 4.5 parts by weight of polyvinylpyrrolidone was dissolved, 46 parts by weight of styrene and 4 parts by weight of 1,3,3-trimethyl-5'-methacryloxymethylindolinospiro naphthooxazine were added. Using an azo series polymerization initiator, polymerization was conducted under nitrogen atmosphere at 70° C. for 16 hours. The resulting dispersion was recovered by filtration, washed repeatedly with methanol and dried to obtain photochromic polymer particles. The obtained particles had an average particle size of 2.0 μm and the maximum particle size was 13 μm. Upon irradiation with ultraviolet light, the polymer particles were colored in deep blue in a short time to show photochromism.

EXAMPLE 29

3.0 g of 1,3,3-trimethyl-9'-methacryloxyindolino spirohaphthooxazine, 15 g of n-butylmethacrylate and 2.0 g of ethylene glycol dimethacrylate were mixed. Using a surface active agent, water-soluble polymerization initiator and 50 ml of water, the mixture was subjected to a typical conventional emulsion polymerization to obtain 18 g of cross-linked polymer particles. 5.0 g of the thus obtained polymer particles and 20 g of a binder (commercially available from Dainippon Ink and Chemicals Inc., Tokyo, Japan under the trade name of "Dicnal K-2551G" were mixed and well stirred to obtain a white composition. The composition was used for the printing of a fabric and was cured at 150° C. for 5 minutes after printing. The print (colorless) was irradiated with ultraviolet light (or sun light). Upon irradiation, the print was colored in blue and a pattern emerged. The coloring-decoloring cycle was able to be conducted many times to prove that the fabric may be used as a chameleon fabric.

COMPARATIVE EXAMPLE 2

Small amount of water, 2.0 g of 1,3,3-trimethylindolinospironaphthooxazine and 10 g of the binder used in Example 29 were mixed and well stirred to obtain a white composition. This composition was utilized for the printing as in Example 29 and the print was subjected to ultraviolet light. However, coloring did not occur at all. This seems to occur because the photochromic compound was not intermiscible with the binder at molecular level.

EXAMPLE 30

Production of Photochromic Soft Contact Lens

A soft contact lens was prepared by pouring a mixture of 94.5 parts by weight of hydroxyethylmethacrylate, 0.5 parts by weight of ethyleneglycol dimethacrylate and 5 parts by weight of 1,3,3-trimethyl-9'-methacryloxyspiro[indoline-2,3'-[3H]-naphtho[2,1-b](1,4)oxazine] into a mold and by conducting cast polymerization. This soft contact lens was colorless and transparent. However, upon irradiating the soft contact lens with sun light or ultraviolet light, the lens was colored in blue. Upon stopping the irradiation the lens was decolored instantly. The coloring-decoloring cycle was able to be repeated many times. The minimum light transmittance of the lens in the colored state was 40%.

EXAMPLE 31

A person actually wore the soft contact lens prepared in Example 30 and went outdoors under the sun light. The person clearly felt that the light transmittance of the lens was reduced to prevent glare.

We claim:

1. A photochromic compound comprising a photochromic spirooxazine compound of the formula:

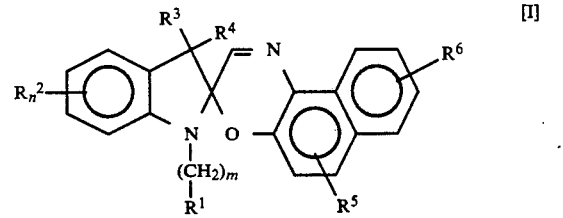

[I]

wherein $R^1$ represents a radial polymerizable unsaturated group selected from the group consisting of acrylic acid ester, methacrylic acid ester, acrylic acid amide, methacrylic acid amide and vinyl benzoic acid ester, or a ring-opening polymerizable organic functional group; $R^2$, $R^5$ and $R^6$ are the same or different, and represent a hydroxyl group, amino group, organic substituted amino group, $C_1$-$C_6$ alkoxyl group, $C_1$-$C_{20}$ alkyl group, halogen, carboxyl group, $C_2$-$C_{10}$ acyl group, nitro group or hydrogen $R^3$ and $R^4$ are the same or different, and represent a $C_1$-$C_{10}$ alkyl group, $C_7$-$C_{12}$ aralkyl group, or $R^3$ and $R^4$ cooperatively represent a $C_6$-$C_8$ alicyclic ring with a spiro carbon atom, norbornyl group or adamantyl group; m is an integer of 1–30; and n is an integer of 0–4,

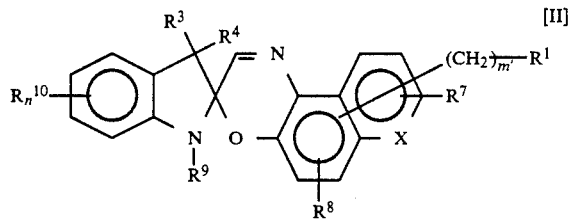

[II]

wherein $R^1$ has the same meaning as in formula [I]; $R^7$, $R^8$ and $R^{10}$ are the same or different, and represent an organic substituted amino group, $C_1$-$C_6$ alkoxy group, $C_1$-$C_{20}$ alkyl group, halogen, carboxyl group, $C_2$-$C_{10}$ acyl group, nitro group or hydrogen; $R^9$ represents a $C_1$-$C_{30}$ alkyl group, phenyl group, substituted phenyl group, $C_7$-$C_{12}$ aralkyl group, $C_7$-$C_{12}$ substituted aralkyl group, $C_1$-$C_{30}$ hydroxyalkyl group, $C_1$-$C_{30}$ aminoalkyl group, $C_4$-$C_{30}$ acryloxyalkyl group, $C_4$-$C_{30}$ acrylamidoalkyl group, $C_5$-$C_{30}$ methacryloxyalkyl group or $C_5$-$C_{30}$ methacrylamidoalkyl group; $R^3$ and $R^4$ have the same meaning as $R^3$ and $R^4$ in formula [I]; X represents N or CH; m' represents an integer of 0–10; and n has the same meaning as in formula [I], with the proviso that when X is nitrogen, the $(CH_2)_{m'}$—$R^1$ group does not bond to this nitrogen atom,

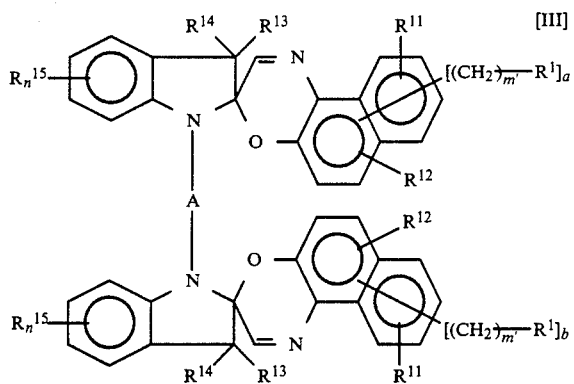

[III]

wherein $R^1$ has the same meaning as in formula [I]; $R^{11}$, $R^{12}$ and $R^{15}$ are the same or different, and represent an organic substituted amino group, $C_1$-$C_6$ alkoxy group, $C_1$-$C_{20}$ alkyl group, halogen, carboxyl group, $C_2$-$C_{10}$ acyl group, hydroxyl group, nitro group, $C_1$-$C_{10}$ hydroxyalkyl group or hydrogen; $R^{13}$ and $R^{14}$ are the same or different, and represent a $C_1$-$C_{10}$ alkyl group, aryl group, $C_7$-$C_{12}$ aralkyl group, or $R^{13}$ and $R^{14}$ cooperatively represent a $C_6$-$C_8$ alicyclic ring with a spiro carbon atom, norbornyl group or adamantyl group; A represents a $C_1$-$C_{30}$ alkylene group, $C_1$-$C_{30}$ alkylene(poly)oxyalkylene group, or $C_8$-$C_{20}$ alkylenearylalkylene group; a and b are the same or different, and are 0 or 1 and (a+b) is 1 or 2; m' and n have the same meaning as in formula [II], respectively or

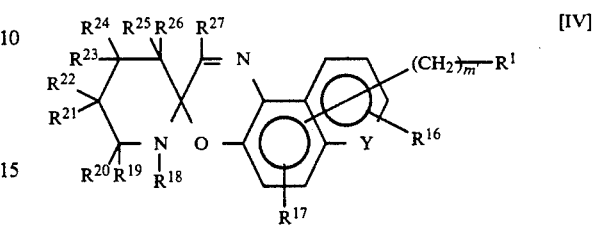

[IV]

wherein $R^1$ has the same meaning as in formula [I]; $R^{16}$ and $R^{17}$ are the same or different, and represent an organic amino group, $C_1$-$C_6$ allkoxyl group, $C_1$-$C_{20}$ alkyl group, halogen, carboxyl group, $C_2$-$C_{10}$ acyl group, cyano group, nitro group or hydrogen; $R^{18}$ is a $C_1$-$C_{30}$ alkyl group, phenyl group, substituted phenyl group, $C_7$-$C_{12}$ aralkyl group, $C_7$-$C_{12}$ substituted aralkyl group, $C_1$-$C_6$ alkoxyl group, carboxyl group, nitro group or hydrogen; $R^{19}$ to $R^{26}$ are the same or different and represent a $C_1$-$C_{30}$ alkyl group, phenyl group, substituted phenyl group, $C_7$-$C_{120}$ aralkyl group, $C_7$-$C_{12}$ substituted aralkyl group, $C_1$-$C_6$ alkoxyl group, carboxyl group, nitro group or hydrogen; $R^{27}$ represents a $C_1$-$C_{30}$ alkyl group, phenyl group, substituted phenyl group, $C_7$-$C_{12}$ aralkyl group, $C_7$-$C_{12}$ substituted aralkyl group, $C_1$-$C_6$ alkoxyl group, carboxyl group, nitro group or hydrogen; Y represents N or C—$R^{16}$ (wherein $R^{16}$ has the same meaning as mentioned above); and m' has the same meaning as in formula [II], with the proviso that when Y is nitrogen, the —$(CH_2)_{m'}$—$R^1$ group does not bond to this nitrogen atom.

2. The photochromic compound of claim 1, which comprises the photochromic spirooxazine compound represented by formula [I].

3. The photochromic compound of claim 1, which comprises the photochromic spirooxazine compound represented by formula [II].

4. The photochromic compound of claim 1, which comprises the photochromic spirooxazine compound represented by formula [III].

5. The photochromic compound of claim 1, which comprises the photochromic spirooxazine compound represented by formula [IV].

6. The photochromic compound of any one of claims 2 to 5 and 1, wherein the ring-opening polymerizable organic functional group is an epoxy ring-opening polymerizable organic functional group.

* * * * *